(12) United States Patent
Suguro et al.

(10) Patent No.: US 7,264,635 B2
(45) Date of Patent: Sep. 4, 2007

(54) ARTIFICIAL KNEE JOINT

(75) Inventors: Toru Suguro, 1201-7, Chibatera-cho, Chuo-ku, Chiba-shi, Chiba (JP); Koichi Kuramoto, Okayama (JP); Keitaro Yamamoto, Okayama (JP)

(73) Assignees: Nakashima Propeller Co., Ltd., Okayama (JP); Toru Suguro, Chiba (JP)

( * ) Notice: Subject to any disclaimer, the term of this patent is extended or adjusted under 35 U.S.C. 154(b) by 0 days.

(21) Appl. No.: 10/360,887

(22) Filed: Feb. 6, 2003

(65) Prior Publication Data

US 2003/0153977 A1 Aug. 14, 2003

(30) Foreign Application Priority Data

Feb. 13, 2002 (JP) .............................. 2002-034935

(51) Int. Cl.
*A61F 2/38* (2006.01)
(52) U.S. Cl. .................................. 623/20.14
(58) Field of Classification Search ............. 623/16.11, 623/18.11, 20.14, 20.15, 20.18, 20.21, 20.23, 623/20.24, 20.26, 20.27, 20.31; 606/87, 606/88, 89
See application file for complete search history.

(56) References Cited

U.S. PATENT DOCUMENTS

| 3,869,731 | A |   | 3/1975  | Waugh et al. |
| 4,081,866 | A |   | 4/1978  | Upshaw et al. |
| 5,133,758 | A | * | 7/1992  | Hollister ....................... 623/20 |
| 5,358,527 | A | * | 10/1994 | Forte ......................... 623/20.27 |
| 5,413,604 | A | * | 5/1995  | Hodge ........................... 623/20 |
| 5,702,460 | A | * | 12/1997 | Carls et al. .................... 623/20 |
| 5,824,105 | A | * | 10/1998 | Ries et al. ..................... 623/20 |
| 6,013,103 | A | * | 1/2000  | Kaufman et al. ......... 623/20.15 |
| 6,056,779 | A |   | 5/2000  | Noyer et al. |
| 6,264,697 | B1| * | 7/2001  | Walker ..................... 623/20.27 |
| 6,344,059 | B1| * | 2/2002  | Krakovits et al. ........ 623/20.31 |
| 6,589,283 | B1| * | 7/2003  | Metzger et al. .......... 623/20.35 |

FOREIGN PATENT DOCUMENTS

| EP | 0 709 075 |   | 5/1996 |
| GB | 33 14 038 |   | 10/1983 |
| WO | WO9730663 | * | 8/1997 |

\* cited by examiner

*Primary Examiner*—Anuradha Ramana
(74) *Attorney, Agent, or Firm*—Koda & Androlia

(57) ABSTRACT

An artificial knee joint including a femoral component to be attached to a femur and a tibial component to be attached to a tibia, wherein in the femur component a medial condyle thereof is thicker than a lateral condyle thereof; in the tibial component, a medial articular surface thereof, which supports the medial condyle of the femur component, is thinner or deeper than a lateral articular surface thereof, which supports the lateral condyle of the femur component; and a joint line joining the lowest points of contact surfaces between the medial and lateral condyles of the femur component and the medial and lateral articular surfaces of the tibial component in a longitudinal cross section in a medial-lateral direction is inclined inward at virtually the same angle over the entire region of an angle of flexion-extension.

1 Claim, 6 Drawing Sheets

ARTIFICIAL KNEE JOINT

BACKGROUND OF THE INVENTION

1. Field of the Invention

The present invention relates to an artificial knee joint that will replace the knee joint.

2. Prior Art

The knee joint is replaced with an artificial knee joint when osteoarthritis, rheumatoid arthritis, or bone tumor is contracted or it is traumatized, etc. This artificial knee joint is a combination of a femoral component having two, a medial and a lateral, condyles; and a tibial component having two, a media and a lateral, articular surfaces, which support the respective two condyles. The condyles and articular surfaces must perform the same movements as with biological knee joints.

More specifically, when an artificial knee joint is attached, the balance between tension and relaxation of the ligaments that are present along the space between the femur and the tibia, particularly the collateral ligaments, needs not to be compromised; and the line that joins the lowest points on the contact surfaces between the medial and lateral condyles and the medial and lateral articular surfaces, which support these condyles so that they can freely slide (hereafter called the joint line), needs to fall inward (inclines inward) approximately 3° over the entire region of the angle of flexion-extension. If ligament balance is compromised, flexion-extension motion will be impaired; and if inward inclination cannot be maintained, adduction-abduction motion whereby the ankles turn out (abduction) during extension and turn inward (adduction) during flexion will not occur, and the same movement as with biological knee joints will not be possible.

FIG. 8A shows a generally known conventional artificial knee joint attached to a right knee and seen from the front when it is flexed 90° (flexed position), The femoral cut line BC is the same distance from the SEA (flexion-extension center axis, which is inherently horizontal) at the medial and lateral condyles, and the component thickness is the same at the medial and lateral condyles. This condylar portion can be used for both right and left knees by simple mechanization of the femoral component. Therefore, there is an advantage in that production is easy and cost is low. There is another advantage in that bone cutting during surgery is simple. However, since the joint line JL is horizontal, there is a disadvantage in that abduction-adduction motion is not induced during flexion-extension and deep flexion is not possible.

In the artificial knee joint shown in FIG. 8B, when the femur is cut, the length of this cut line BC from the SEA is set to be longer at the medial condyle than the lateral condyle, and the joint line JL is set to be inclined inward, thus being similar to a biological knee joint. However, because the medial and lateral supporting surfaces of the tibial component are at the same height, the medial condyle rises (resulting in that the SEA becomes inclined outwardly), and the medial collateral ligament on this side elongates, thus causing excess tension and making smooth flexion-extension impossible. Therefore, in some cases part of the ligament is also cut. However, when this is done, the control function of the ligament is not realized during flexion-extension and flexion-extension motion becomes awkward. In addition, bleeding occurs, prolonging surgery time and increasing the stress on the patient.

The artificial knee joint shown in FIG. 8C is disclosed in Patent Application National Publication No. 11-504226, and it is to correct the above-described problems. Excess tension on a ligament is corrected by making the medial condyle of the femoral component thinner than the lateral condyle in order to lower the medial condyle. However, although ligament balance returns to normal, there is a reduction in the degree of forward inclination of the joint line JL. Therefore, adduction-abduction motion during flexion-extension does not occur, and deep flexion is not possible. Furthermore, in this prior art, the posterior part of the medial condyle is made thinner, inducing adduction during the final stages of flexion-extension. However, forward inclination of the joint line JL must be maintained throughout all of flexion-extension. Accordingly, adduction motion, particularly, during flexion-extension does not occur and smooth flexion-extension is inhibited.

SUMMARY OF THE INVENTION

In light of the above-described problems, the present invention provides an artificial knee joint that comprises a femoral component to be attached to a femur and a tibial component to be attached to a tibia, wherein, in the femur component, the thickness of a medial condyle thereof is made larger than that of a lateral condyle thereof, the thickness of the medial condyle corresponding to the length between the cut line (BC) that is parallel to a flexion-extension center axis (SEA) and the lower end of the medial condyle of the femoral component;

in the tibial component, a medial articular surface thereof, which supports the medial condyle of the femur component, is made thinner or deeper than the lateral articular surface thereof, which supports the lateral condyle of the femur component; and a joint line joining lowest points of contact surfaces between the medial and lateral condyles and the medial and lateral articular surfaces in a longitudinal cross section in a medial-lateral direction is inclined inward at virtually the same angle over the entire region of an angle of flexion-extension; and wherein a maximum thickness line that longitudinally links points of maximum thickness of the medial condyle turns outward toward the front of the femur component, thus making the distance between the maximum thickness line of the medial condyle and the maximum thickness line of the lateral condyle narrower, and forming a toe-in configuration;

a pivot base is formed in the posterior part of the medial articular surface of the tibial component so that when medial condyle of the femoral component enters therein the pivot base restricts further backward shifting of the medial condyle; and a posterior part of a lowest point line that longitudinally links the lowest points of the lateral articular surface of the tibial component turns inward around to a pivot point which is at the center of the pivot base.

In the artificial knee joint of the present invention, the medial condyle of the femoral component, which corresponds to the length between the cut line (BC) that is parallel to a flexion-extension center axis (SEA) and the lower end of the medial condyle of the femur component, is made thicker than the lateral condyle, and the lateral articular surface of the tibial component is made thinner or deeper than the medial articular surface. Accordingly, the joint line, which is a straight line, inclines inwardly, and it is easy to acquire a balance between tension and relaxation of ligaments, particularly the medial collateral ligaments, and smooth flexion-extension becomes possible. In addition, adduction-abduction motion is induced and deep flexion also becomes possible as a result of the inward inclination of the straight joint line. Thus, movement approximating that of a biological knee joint is possible. In this case, inclination of the joint line should be the same as a biological knee joint, which is 1 to 10°, preferably 2 to 5°.

Furthermore, in the artificial knee joint of the present invention, the line of maximum thickness that longitudinally links the points of maximum thickness in the medial-lateral direction of the medial condyle is set so as to turn outward toward the front. As a result, in conjunction with the above-described forward inclination of the joint line, the adduction motion of the knee joint during flexion is further induced, and smooth flexion-extension operation is obtained.

Moreover, in the present invention, a pivot base is formed in a posterior part of the medial articular surface so that the medial condyle is inserted therein and so that the pivot base restricts further backward shifting of the medial condyle; and a posterior part of a lowest point line that longitudinally links lowest points of the lateral articular surface turns inward around a pivot point that is set at a center of the pivot base. Accordingly, the adduction motion is further facilitated and deep flexion becomes possible.

Though pre-determined cutting of both the femur and the tibia is generally necessary for attaching an artificial knee joint, with the knee joint of the present invention, surgery for such can be done easily because the femur can be cut parallel to SEA (flexion-extension center axis) and the tibia can be cut perpendicular to a mechanical axis. The SEA is an axis that becomes the center of rotation when the femur flexes and extends; and the SEA is perpendicular to the mechanical axis, which is substantially perpendicular and joins the ankle and center of the hip joint, thus being horizontal.

DETAILED DESCRIPTION OF THE INVENTION

Embodiments of the present invention will be described below with reference to the accompanying drawings.

Figure 1:
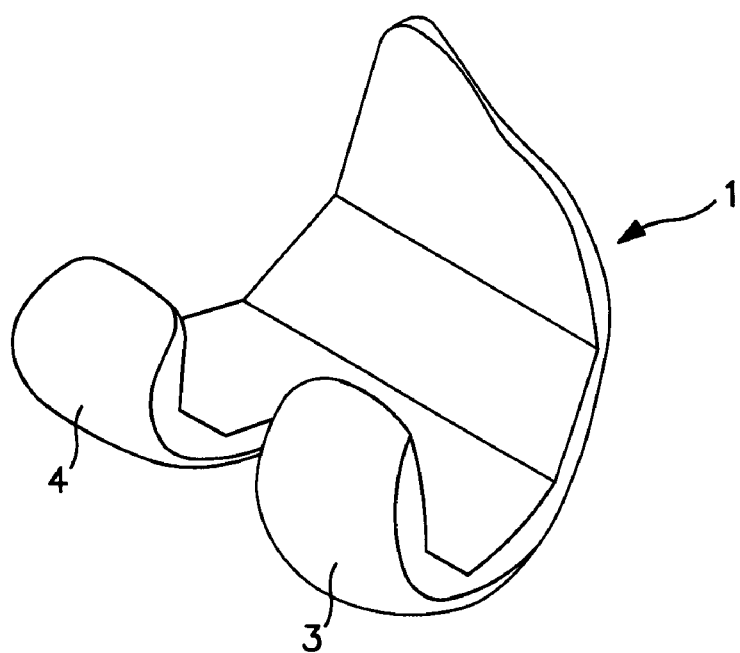
FIG. 1 is a perspective view of a femoral component according to one example of the present invention.
Figure 2:
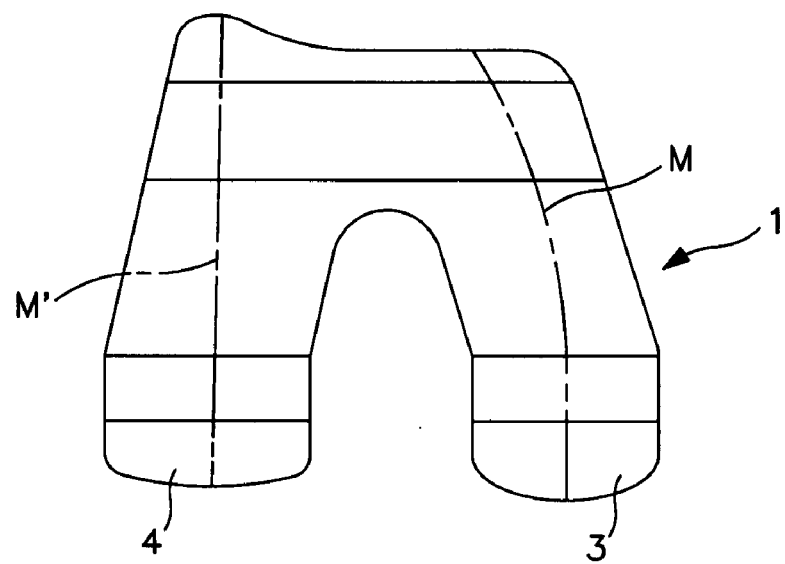
FIG. 2 is a bottom view thereof.
Figure 3:
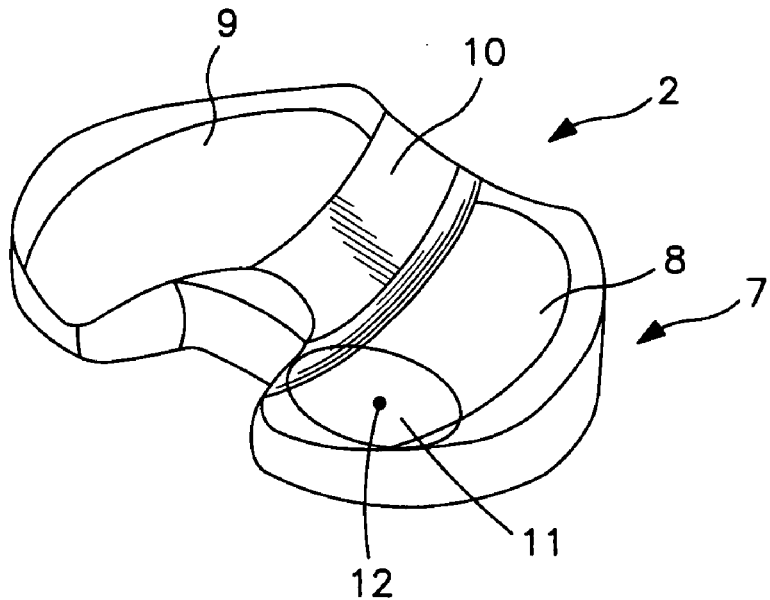
FIG. 3 is a perspective view of a tibial component according to one example of the present invention
Figure 4:
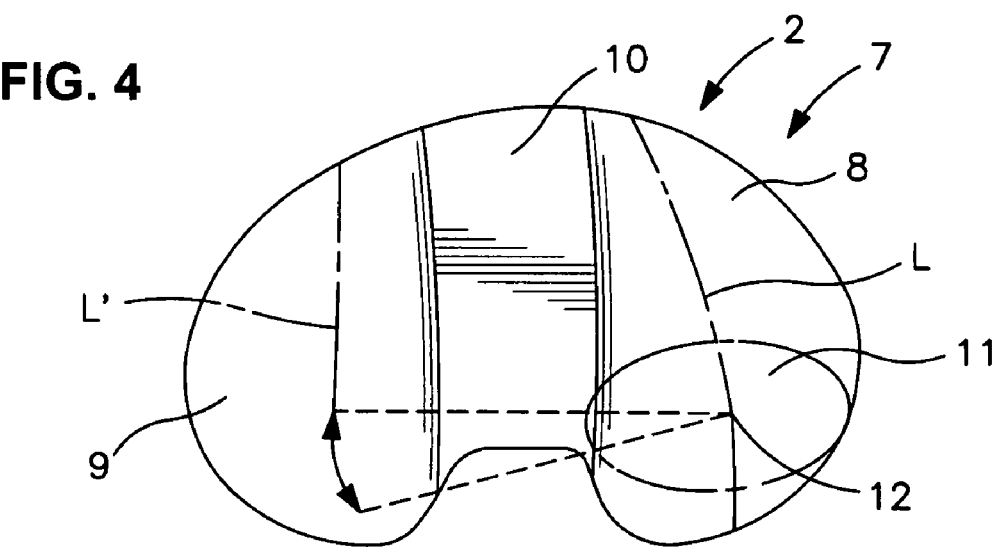
FIG. 4 is a top view thereof.
Figure 5:
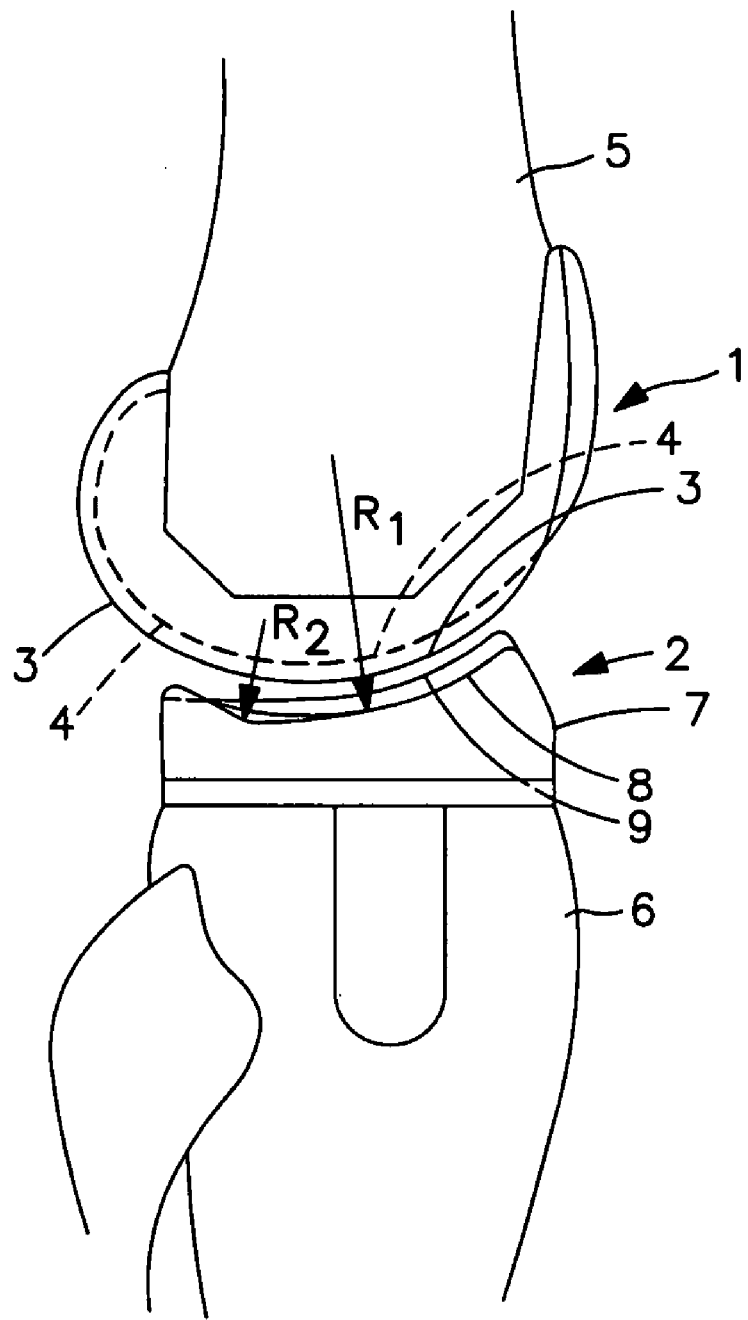
FIG. 5 is a side view of a knee joint to which the femoral component and the tibial component according to one example of the present invention are attached.

The artificial knee joint comprises a combination of a femoral component 1 and a tibial component 2. Of these, the femoral component 1 is made from a biocompatible metal, such as titanium alloy, etc. An inlet shape is cut out from the center of the posterior part so that from the side view a medial condyle 3 and a lateral condyle 4 form a substantially round shape, that is, a substantially C shape with the medial condyle 3 thicker than the lateral condyle 4 over an entire region of an angle of flexion-extension as shown in FIG. 5. The femoral component 1 is attached to the distal end of femur 5. There is also a type that is called the PS (posterior stabilized) type where part of the cut-away part is covered by a box to restrict specific movement of the other member, but this is functionally the same. In this case, when the medial condyle 3 and lateral condyle 4 are viewed from the longitudinal direction, their contour makes a convex shape, and this convex shape connects with tendons longitudinally.

In contrast to the above, the tibial component 2 is obtained by forming an insert 7 made from a medical resin, such as ultra-high-molecular-weight polyethylene, etc., on a base of a biocompatible metal and is attached to the proximal end of tibia 6. Low protuberances 10 are formed at intervals on the top surface of insert 7 between a medial articular surface 8 and a lateral articular surface 9, which support medial condyle 3 and lateral condyle 4, respectively, of above-described femoral component 1. These two articular surfaces 8 and 9 are formed in a concave shape which substantially follows the contour shape of medial condyle 3 and lateral condyle 4, with this concave shape spreading out longitudinally. In this case, the top and bottom planes of projection of medial and lateral condyles 3 and 4 and medial and lateral articular surfaces 8 and 9 are set up almost the same.

The femur 5 and tibia 6 should flex and extend relatively with flexion-extension of the knee. In the above-described artificial knee, this movement is accomplished by the sliding movement that accompanies the revolving and sliding movements of the medial and lateral condyles 3 and 4 on the medial and lateral articular surfaces 8 and 9. The angle of flexion-extension is 100 to 130°; and revolution is the main movement during the initial stages, and sliding becomes the main movement during the final stages. However, each of these movements is controlled by ligament groups such as the cruciate ligaments and collateral ligaments so that the medial and lateral condyles 3 and 4 do not slip (dislocate) from medial and lateral articular surfaces 8 and 9.

Figure 6:
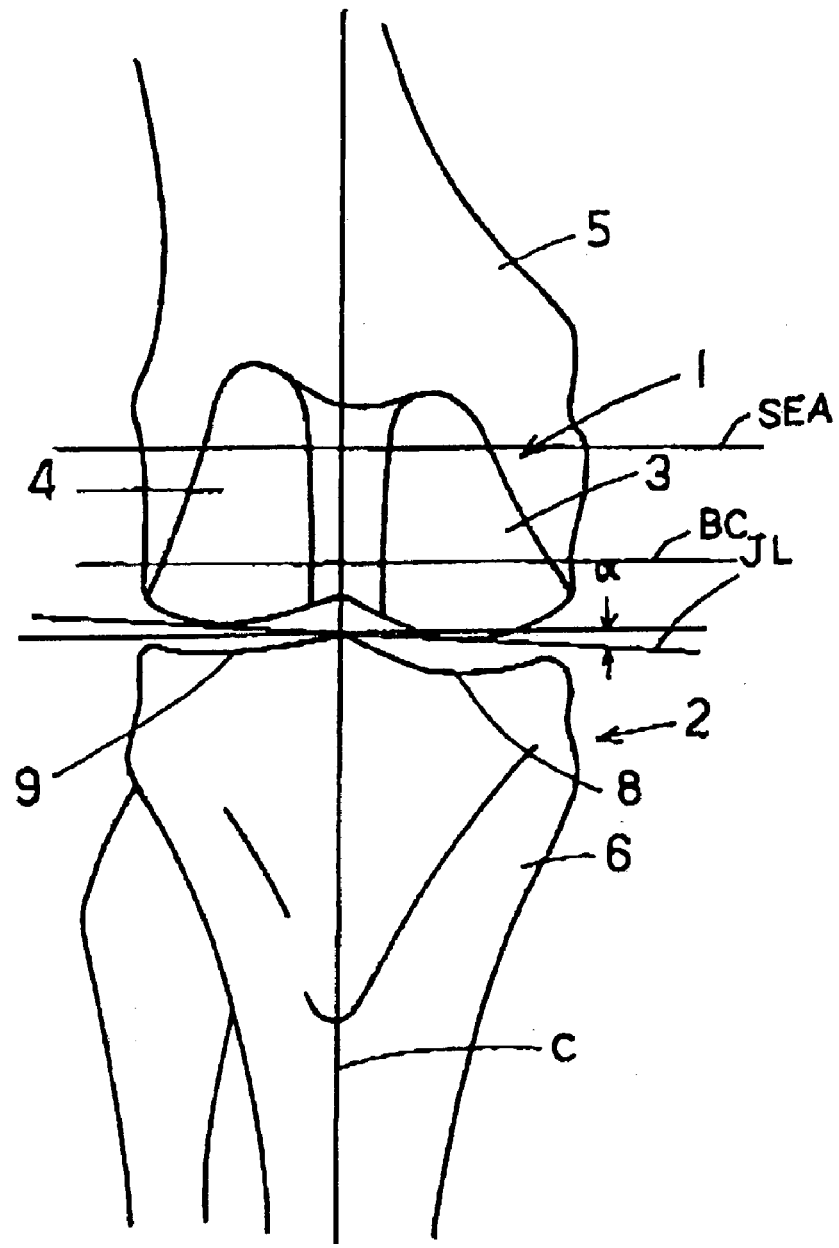
FIG. 6 is a rear view during extension of a knee joint to which the femoral component and the tibial component according to one example of the present invention are attached.
Figure 7:
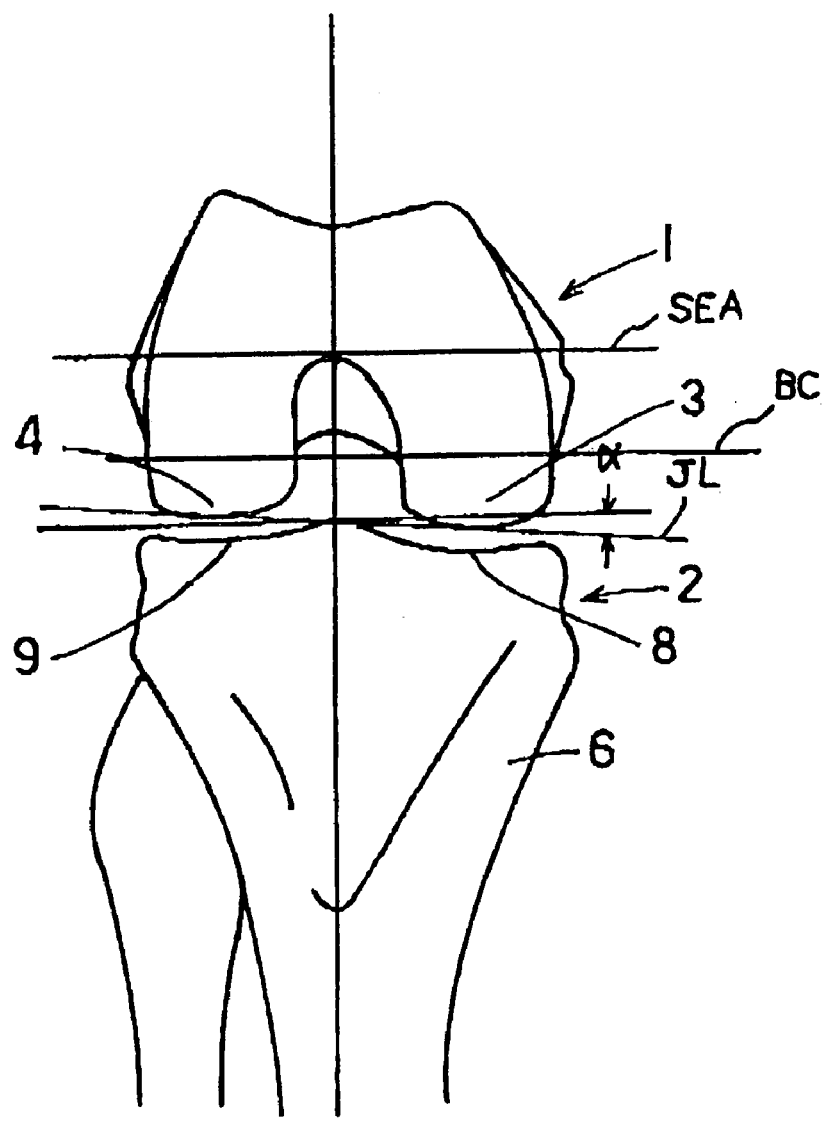
FIG. 7 is a rear view during 90° flexion of a knee joint to which the femoral component and the tibial component according to one example of the present invention is attached.
Figure 8A:
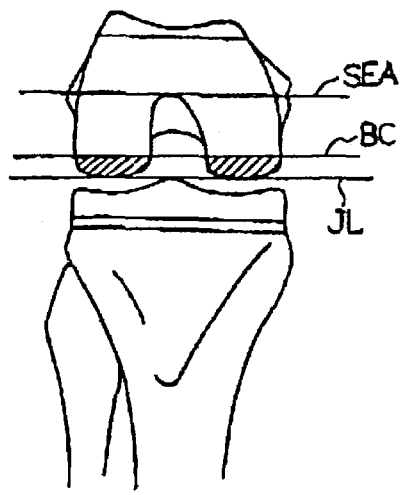
FIGS. 8A, 8B and 8C are explanatory illustrations seen from the front when the right knee is flexed 90° in conventional artificial knee joints.
Figure 8B:
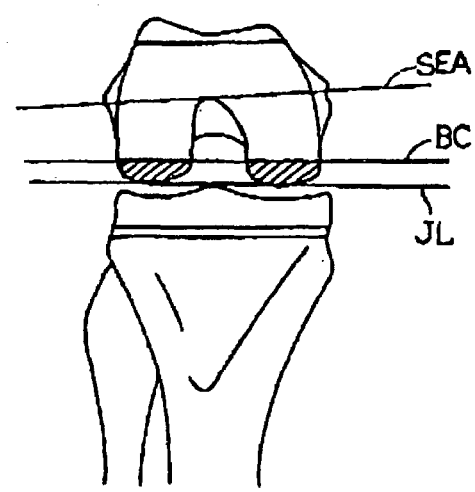
Figure 8C:
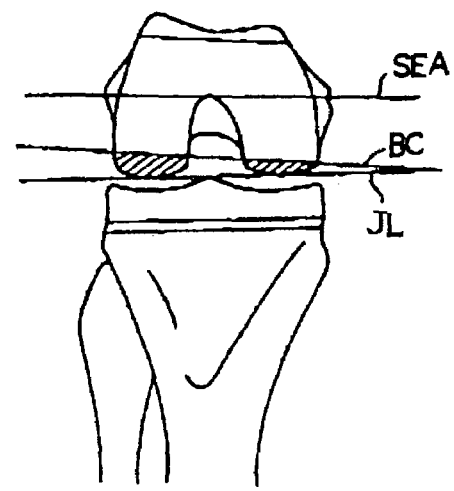

In the present invention, the thickness of the medial condyle 3 and lateral condyle 4 of the femoral component 1 is set so that the medial condyle 3 is thicker than the lateral condyle 4 as shown in FIG. 5. Moreover, so as to correspond to this, the thickness of the medial articular surface 8 and lateral articular surface 9 on the insert 7 of the tibial component 2 is set so that the medial articular surface 8 is thinner or deeper than the lateral articular surface 9. In other words, there is a difference in the level around the outside of medial condyle 3 and lateral condyle 4 and medial articular surface 8 and lateral articular surface 9 so that the balance between tension and relaxation of the collateral ligaments is not compromised. Joint line JL, which joins the lowest points on the contact surfaces between condyles 3 and 4 and articular surfaces 8 and 9, which hold these respective condyles, are set to be lower on the inside, that is, they are inclined inward with respect to the mechanical axis. This difference in level is not difficult to form because it can be made during the component production. With the above settings, the cut line BC of the femur is parallel to the SEA, and the tibia is cut perpendicular to the mechanical axis C shown in FIG. 6.

The reason for the above setting is that this is how biological knee joints are; and by making the artificial knee the same like this, the balance between tension and relaxation of the collateral ligaments will not be compromised, and knee function (flexion-extension) will not be diminished after replacement. The angle of inward inclination α of the joint line JL in this case should be the same as that of a biological knee joint, 1 to 10°, preferably 2 to 5°. In addition, in the above example, the curvature radius of the convex surface of medial condyle 3 is set to be smaller than that of lateral condyle 4; and so as to correspond to this, the curvature radius of the concave surface of medial articular surface 8 is smaller than that of lateral articular surface 9.

Moreover, in the above example, a maximum thickness line M, which links the points of maximum thickness of the medial condyle 3 longitudinally, turns outward toward the front so that its distance from a maximum thickness line M', which links the points of maximum thickness of lateral condyle 4 longitudinally, becomes narrower (and accordingly, lines L and L' that correspond to the maximum thickness and diameter lines are formed on medial and lateral articular surfaces 8 and 9); and thus a so-called "to-in" is established. This setting is made because when this is done, the adduction motion of the tibia 6 side is further induced during flexion.

Furthermore, in the above example, in the posterior part of medial articular surface 8 is formed with a pivot base 11 into which the medial condyle 3 is inserted and which restricts further backward shifting of the medial condyle. More specifically, while the medial articular surface 8 forms a concave surface of radius $R_1$ when viewed from the side, a concave surface of radius $R_2$ ($<R_1$) is formed in the posterior part of the concave surface of radius $R_1$ so that the concave surface of radius $R_2$ serves as the pivot base 11. In this case, the lowest surface of pivot base 11 is set up so that it is the same or slightly lower than the lowest surface of medial articular surface 8.

On the other hand, it is preferable that some of the concave surface of radius $R_1$ remain behind the pivot base 11. This is because this is the portion that works when in a standing position (during extension); and therefore, this standing position is stabilized by the presence of this remaining concave surface. When the medial condyle 3 enters into the pivot base 11 during the final stages of flexion, further backward shifting of medial condyle 3 is restricted so that there is only relative sliding motion. Consequently, the adduction motion is facilitated, smooth flexion is realized, and deep flexion becomes possible. At this time, by way of setting the posterior part of the lowest point line L', which links the lowest points of the lateral articular surface 9 longitudinally, at a further backward location than the pivot point 12, which is into center of the pivot base 11, this adduction motion is further induced, and a large angle of flexion can be obtained.

When the above-described artificial knee joint is attached, joint line JL is inclined so that it is lower on the inside; and as a result, behavior during flexion and extension of the knee naturally approximates that of a biological knee joint and the balance between tension and relaxation of ligaments, particularly collateral ligaments, is not compromised. Consequently, there will be no dysfunction, even if some of these ligaments are not detached during surgery, and the stress on the patient will be alleviated. Moreover, the distance between the maximum diameter lines M and M' of the medial and lateral condyles will be brought to toe-in, the adduction-abduction motion during flexion-extension will be induced, and smooth flexion-extension operation will be realized.

The epiphyses of femur 5 and tibia 6 must be cut during the attachment of the artificial knee. In the present invention, such a surgery is expected to be simple because, as previously described, the femur can be cut parallel to the SEA and the tibia can be cut perpendicular to the machine axis.

According to the artificial knee joint of the present invention, a balance between tension and relaxation of collateral ligaments when the joint is attached can be acquired for smooth flexion-extension, and abduction motion during extension and adduction motion during the final stages of flexion-extension can be induced so that smooth movement becomes possible and deep flexion also becomes possible. From this point, the same movement as with biological knee joints can be realized.

The invention claimed is:

1. An artificial knee joint comprising a femoral component to be attached to a femur and a tibial component to be attached to a tibia wherein:

in the femoral component, a thickness of a medial condyle thereof is made larger than that of a lateral condyle thereof, said thickness corresponding to a length between a cut line of a femur that is parallel to a horizontal flexion-extension center axis and a lower end of said medial condyle of said femoral component;

in the tibial component, a medial articular surface thereof, which supports the medial condyle of said femoral component, is made deeper than a lateral articular surface thereof, which supports the lateral condyle of said femoral component; and a joint line joining lowest points of contact surfaces between the medial and lateral condyles and the medial and lateral articular surfaces in a longitudinal cross section in a medial-lateral direction is inclined inwardly at virtually the same angle over the entire region of an angle of flexion-extension;

and wherein a maximum thickness line that longitudinally links points of maximum thickness of the medial condyle of said femoral component turns outward toward a front of said femoral component, thus making a distance between the maximum thickness line of the medial condyle and a maximum thickness line of the lateral condyle smaller toward the front of said femoral component;

lowest point lines that, respectively, longitudinally link lowest points of the medial and lateral articular surfaces of said tibial component are, respectively, set to correspond with said maximum thickness lines of said femoral component in terms of direction and distance in between;

a pivot base is formed in a posterior part of the medial articular surface of said tibial component so that when the medial condyle of said femoral component enters therein the pivot base restricts further backward shifting of the medial condyle, a lowest point of a bottom of the pivot base being at a level that is the same as or lower than a lowest point of the medial articular surface; and a posterior part of a lowest point line that longitudinally links lowest points of the lateral articular surface of said tibial component turns inward around a pivot point which is at a center of said pivot base.

* * * * *